(12) United States Patent
Yin et al.

(10) Patent No.: US 11,407,698 B2
(45) Date of Patent: Aug. 9, 2022

(54) SYNTHESIS METHOD FOR HIGHLY SELECTIVE 2-METHYLALLYL CHLORIDE AND SYNTHESIS REACTOR THEREOF

(71) Applicants: ZHEJIANG UNIVERSITY, Zhejiang (CN); ZHEJIANG HUANGMA TECHNOLOGY CO., LTD., Zhejiang (CN)

(72) Inventors: Hong Yin, Hangzhou (CN); Zhirong Chen, Hangzhou (CN); Xinrong Wang, Shaoxing (CN); Weisong Wang, Shaoxing (CN); Yuanrong Yu, Shaoxing (CN); Shengli Wang, Shaoxing (CN); Yuefen Wang, Shaoxing (CN); Zhenqiang Ma, Shaoxing (CN); Xingjun Zhao, Shaoxing (CN); Jianfang Qian, Shaoxing (CN)

(73) Assignees: ZHEJIANG UNIVERSITY, Zhejiang (CN); ZHEJIANG HUANGMA TECHNOLOGY CO., LTD., Zhejiang (CN)

( * ) Notice: Subject to any disclaimer, the term of this patent is extended or adjusted under 35 U.S.C. 154(b) by 0 days.

(21) Appl. No.: 16/759,931

(22) PCT Filed: Oct. 10, 2018

(86) PCT No.: PCT/CN2018/109596
§ 371 (c)(1),
(2) Date: Apr. 28, 2020

(87) PCT Pub. No.: WO2019/144647
PCT Pub. Date: Aug. 1, 2019

(65) Prior Publication Data
US 2021/0179520 A1    Jun. 17, 2021

(30) Foreign Application Priority Data

Jan. 29, 2018  (CN) .......................... 201810085845.3
Feb. 5, 2018   (CN) .......................... 201810109001.8

(51) Int. Cl.
*C07C 17/10* (2006.01)
*C07C 21/067* (2006.01)
(Continued)

(52) U.S. Cl.
CPC ............... *C07C 17/10* (2013.01); *B01J 12/00* (2013.01); *B01J 19/0093* (2013.01);
(Continued)

(58) Field of Classification Search
None
See application file for complete search history.

(56) References Cited

U.S. PATENT DOCUMENTS

| 2,604,439 A | 7/1952 | Nixon |
| 4,870,220 A * | 9/1989 | Jabrik ..................... C07C 17/10 570/234 |

(Continued)

FOREIGN PATENT DOCUMENTS

| CN | 1030407 | 11/1995 |
| CN | 1288119 | 3/2001 |

(Continued)

OTHER PUBLICATIONS

CN1456544A, English translation, Nov. 19, 2003, pp. 1-11 (Year: 2003).*

(Continued)

*Primary Examiner* — Jennifer A Leung
(74) *Attorney, Agent, or Firm* — Maschoff Brennan

(57) ABSTRACT

The present invention relates to a synthesis method and synthesis reactor of high-selectivity 2-methylallyl chloride (Continued)

by taking isobutylene and chlorine gas as raw materials and performing a gas-phase chlorination reaction in a microchannel reactor with a cooling surface. The isobutylene and the chlorine gas are reacted in a T-shaped microchannel reactor, and the mixing speed is extremely fast. Meanwhile, the huge heat exchange area per unit volume can ensure that the reaction proceeds stably at a substantially constant temperature and has good controllability. Therefore, side reactions caused by excessive local temperature can be effectively suppressed, the reaction selectivity is high, and no coking phenomenon occurs.

6 Claims, 1 Drawing Sheet

(51) Int. Cl.
    *B01J 19/24*     (2006.01)
    *B01J 12/00*     (2006.01)
    *B01J 19/00*     (2006.01)

(52) U.S. Cl.
    CPC ....... *B01J 19/2415* (2013.01); *B01J 19/2425* (2013.01); *B01J 2219/00094* (2013.01); *B01J 2219/00247* (2013.01); *B01J 2219/00792* (2013.01); *B01J 2219/00869* (2013.01); *B01J 2219/00873* (2013.01)

(56) References Cited

U.S. PATENT DOCUMENTS

| | | | | |
|---|---|---|---|---|
| 7,098,344 | B2* | 8/2006 | Koop | ................... B01F 5/0256 |
| | | | | 548/303.7 |
| 10,512,889 | B2* | 12/2019 | Okamoto | .................. B81B 1/00 |
| 2003/0003024 | A1* | 1/2003 | Zech | ................... B01F 13/0059 |
| | | | | 422/400 |
| 2007/0212267 | A1* | 9/2007 | Organ | .................... C07C 45/68 |
| | | | | 422/130 |
| 2009/0142845 | A1* | 6/2009 | Benali | ................. B01J 19/0093 |
| | | | | 436/8 |
| 2016/0129417 | A1* | 5/2016 | Aimone | ................... B01J 19/02 |
| | | | | 422/198 |

FOREIGN PATENT DOCUMENTS

| | | |
|---|---|---|
| CN | 1456544 A | 11/2003 |
| CN | 200995994 Y | 12/2007 |
| CN | 101182279 | 5/2008 |
| CN | 202044960 | 11/2011 |
| CN | 106608811 A | 5/2017 |
| CN | 108164388 A | 6/2018 |
| DE | 3402446 | 7/1985 |
| GB | 684577 A | 12/1952 |

OTHER PUBLICATIONS

CN Office Action and Search Report dated Jan. 3, 2020 as received in Application No. 201810109001.8.

* cited by examiner

SYNTHESIS METHOD FOR HIGHLY SELECTIVE 2-METHYLALLYL CHLORIDE AND SYNTHESIS REACTOR THEREOF

TECHNICAL FIELD

The present invention relates to a chlorination reaction of organic matters and a device therefor, and belongs to the field of organic synthesis reactions.

BACKGROUND ART 2-methyl-3-chloroallyl is an important intermediate for organic synthesis and is widely used in medicine, pesticides, perfume monomers, polymer materials and other fields.

2-methyl-3-chloroallyl is usually obtained by a gas-phase chlorination reaction of isobutylene with chlorine gas.

Early chlorination reactions are carried out in a tubular reactor with a cooling jacket. The reaction temperature is below 100° C., the pressure is a normal pressure, and the reaction residence time is in a range of 0.5 seconds to several seconds. In order to avoid deep chlorination side-reactions, it is usually necessary to maintain an excess of isobutylene. The two raw materials are added to a reaction tube by spraying.

In order to avoid temperature fluctuations in the reaction process, DE3402446 proposes that a certain amount of oxygen can be added during the reaction process. However, this method is prone to produce a mixture of excessive isobutylene and oxygen, thereby causing a safety risk. For this purpose, CN1030407 proposes a method for injecting chlorine gas at a plurality of positions in a length direction of a jacketed cooling reaction tube to solve the problem of temperature fluctuations, but requires to ensure that the flow rate of the chlorine gas reaches 150~260 m/s, and the reaction selectivity is up to 86.5%.

The tubular reactor has a small heat exchange area per unit volume. Therefore, a significant temperature distribution occurs in the length direction of the reaction tube, and local high temperatures can lead to increased side reactions and decreased reaction selectivity.

In view of the problems in the tubular reactor, CN1288119 employs concentric nozzles and meanwhile removes the reaction heat in such a manner that chlorinated reactants circulate to be in direct contact with a reaction gas for cooling, but no selectivity data is given.

CN101182279 employs a plurality of concentric spray heads and meanwhile removes the reaction heat in such a manner that chlorinated reactants circulate to be in direct contact with a reaction gas for cooling. The highest selectivity given in the examples is 85.9%.

The disadvantage of the above chlorination technology is that a reaction site has no cooling surface and the temperature cannot be controlled. Therefore, there are many side reactions and low selectivity, and the nozzles or spray heads may be blocked due to excessive chlorination and coking.

In view of the problem of easy coking of nozzles, CN202044960 proposes to use flat nozzles in the utility model patent. At the same time, the reaction heat is removed in such a manner that chlorination reactions circulate to be in direct contact with the reaction gas. However, the patent neither provides examples to demonstrate that the coking problem is solved, and there is no example to demonstrate that the product content in the reaction solution reaches 88%.

SUMMARY OF THE INVENTION

In view of the problems existing in the synthesis of 2-methylallyl chloride reported in literatures, the present invention proposes a method for synthesizing high-selectivity 2-methylallyl chloride. Special equipment is adopted in this reaction, and the reaction process is stable, with good controllability; the reaction selectivity is high, accompanied with few side reactions, and no coking phenomenon will occur.

The present invention also provides the synthesis reactor.

A method for synthesizing high-selectivity 2-methyl-3-chloroallyl, which is used for synthesizing 2-methyl-3-chloroallyl by taking isobutylene and chlorine gas as raw materials, and performing a chlorination reaction in a synthesis reactor with a cooling surface, and is characterized in that: the synthesis reactor is a synthesis reaction tube with an isobutylene inlet tube and a chlorine gas inlet tube; the isobutylene and the chlorine gas form a mixed raw material and enter the synthesis reaction tube for a gas-phase chlorination reaction; the chlorination reaction temperature is 0~30° C.; the isobutene inlet tube, the chlorine gas inlet tube and the synthesis reaction tube have a diameter of 0.2~0.5 mm, respectively; and the cooling surface of the synthesis reactor has a heat exchange area of 8000~20000 $m^2/m^3$ based on the actual reaction volume.

A slightly excessive amount of isobutylene is added in the chlorination reaction.

A molar ratio of the isobutylene to the chlorine gas is preferably 1.005~1.02: 1.

The chlorination reaction residence time is 0.1~1 second.

A high-selectivity 2-methyl-3-chloroallyl synthesis reactor is characterized in that: the synthesis reactor is a synthesis reaction tube with an isobutylene inlet tube and a chlorine gas inlet tube and is wrapped in a cooling jacket; and the isobutylene inlet tube, the chlorine gas inlet tube, and the synthesis reaction tube are connected in a tee form.

The isobutylene inlet tube, the chlorine gas inlet tube, and the synthesis reaction tube are connected in a T-shape or a Y-shape.

The isobutene inlet tube and the chlorine gas inlet tube are connected in a U-shape, and the upper end of the synthesis reaction tube is connected to the U-shaped bottom.

The isobutene inlet tube, the chlorine gas inlet tube and the synthesis reaction tube have a diameter of 0.2~0.5 mm, respectively; and the cooling surface of the synthesis reactor has a heat exchange area of 8000~20000 $m^2/m^3$ based on the actual reaction volume.

A synthesis reactor assembly of high-selectivity 2-methyl-3-chloroallyl includes several above-mentioned synthesis reactors, and the cooling jackets of the several synthesis reactors are communicated with each other.

The several synthesis reactors are fixed side by side in the same cooling jacket.

The inventors of the present invention have found through researches that the gas-phase chlorination reaction of isobutene is a strongly exothermic reaction. Under the equimolar ratio of isobutylene to chlorine gas, the adiabatic temperature rise of the complete reaction can reach 440° C., and the higher the reaction temperature, the faster the reaction, and the more side reactions, which easily leads to a coking problem. Therefore, in order to control the reaction temperature and improve the reaction selectivity, it is necessary to effectively control the reaction temperature. Theoretical calculations and experimental verifications show that when the heat transfer area based on the actual reaction volume reaches more than 8000 $m^2/m^3$, and the reaction takes place at 0~30° C. The reaction can be performed at a substantially constant temperature, and the hot spot temperature does not exceed a set temperature by 3° C. To achieve such a large heat exchange area per unit reaction volume, it is only possible to reduce the diameter of a reaction channel to be less than 0.5 mm. The specially designed synthesis reactor of the present invention, also called a microchannel reactor, can just meet the requirements. In order to promote the mixing of isobutylene and chlorine gas, a T-type microchannel reactor is more suitable. To ensure the selectivity, a slightly excessive amount of a molar ratio of the isobutene is suitable. In order to ensure sufficient chlorine gas reaction, the reaction residence time is preferably 0.1~1 second.

In the process of the present invention, the reaction temperature is controlled, the heat exchange area is increased, and the chlorination reaction is performed in a small reaction tube, thereby ensuring a constant reaction temperature, no coking and good selectivity.

The microchannel reactor designed to realize the process of the present invention performs the chlorination reaction of isobutylene, the reaction process is stable, with good controllability; the reaction selectivity is high, with few side reactions, and no coking phenomenon will occur.

Because the microchannel reactor of the present invention performs the reaction in the small reaction tube, a plurality of synthetic reactors can be combined together in the production, and share the same cooling jacket, thereby improving the reaction efficiency.

Reference symbols represent the following components: 1-cooling jacket; 2-chlorine gas inlet tube; 3-isobutylene inlet tube; 4-reaction tube; 5-reaction product outlet tube.

DETAILED DESCRIPTION

The technical solution of the present invention is further described below with reference to the drawings and examples.

Figure 1:
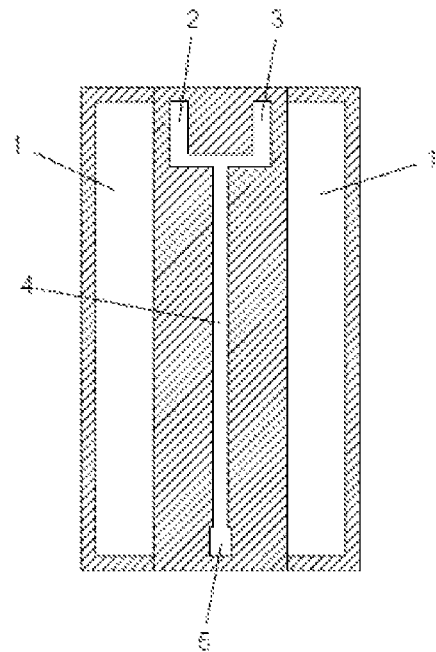
FIG. 1 is a schematic structural diagram of a synthesis reactor according to the present invention.

As shown in FIG. 1, the present invention relates to a synthesis reactor with a cooling jacket 1. The reactor is an elongated reaction tube 4. A raw chlorine gas inlet tube 2 and an isobutylene inlet tube 3 are connected to an upper port of the reaction tube 4, and a reaction product outlet tube 5 is connected to a lower port of the reaction tube 4. According to the present invention, the chlorine gas inlet tube 2, the isobutylene inlet tube 3 and the reaction tube 4 are connected (e.g., connected in a tee shape) just by ensuring that the two raw materials enter the one end of the reaction tube 4 at the same time for a mixed reaction. A product outlet is formed in the other end of the reaction tube 4. Preferably, the chlorine gas inlet tube 2, the isobutylene inlet tube 3 and the reaction tube 4 are T-shaped or Y-shaped.

Figure 2:
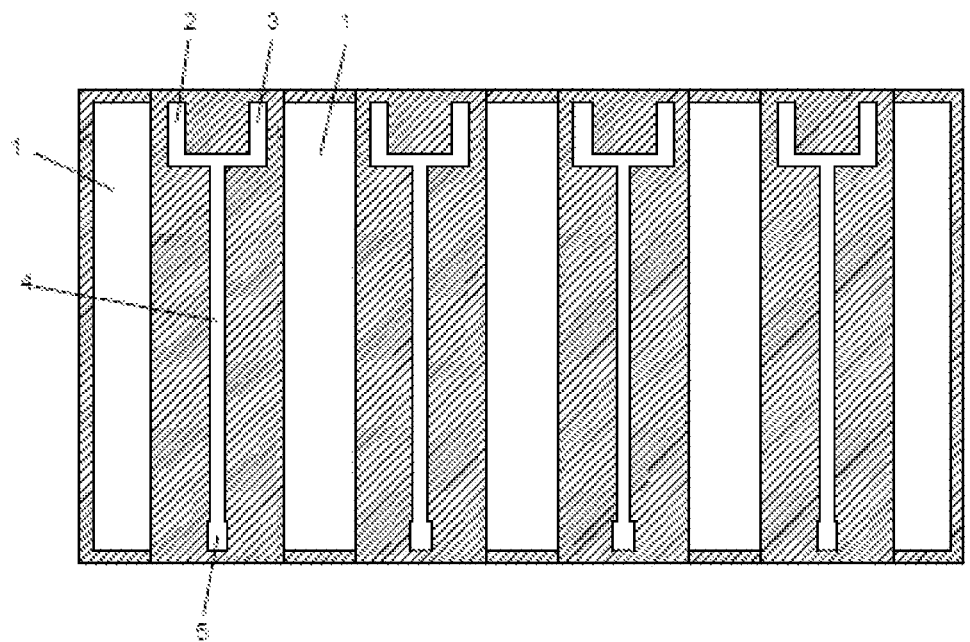
FIG. 2 is a schematic structural diagram of a synthesis reactor assembly of the present invention.

As shown in FIG. 2, a plurality of synthesis reactors of the present invention are connected in a combined manner. Each reactor is an independent reaction tube 4, with an independent chlorine gas inlet tube 2, isobutene inlet tube 3 and reaction product outlet tube 5. A plurality of reactors share the same cooling jacket 1, which is equivalent that a plurality of synthesis reactors of the present invention are fixed side by side in the same cooling jacket, thereby effectively using the space and energy, and improving the reaction efficiency.

EXAMPLE 1

Isobutene and chlorine gas are introduced respectively into the microchannel reactor shown in FIG. 1 (the channel diameter is 0.2 mm, and the heat exchange area calculated based on the actual reaction volume is 20000 $m^2/m^3$). By adjusting and controlling the flows of isobutene and chlorine gas, the reaction residence time reaches 1 second. A molar ratio of the isobutylene to the chlorine gas is 1.005:1, and the reaction temperature is controlled to 0° C. by freezed brine. After 30 minutes of stable operation, a liquid product is sampled from an outlet of the reactor, and the composition of the liquid product is analyzed as the following mass content: 89.6% of 2-methylallyl chloride, 2.3% of chloro-tert-butane, 1.3% of isobutenyl chloride, 5.6% of dichloro-tert-butane, and 1.2% of dichloro-isobutene. Therefore, the selectivity of the calculated 2-methylallyl chloride is calculated as 91.4%.

EXAMPLE 2

Isobutene and chlorine gas are introduced respectively into the microchannel reactor shown in FIG. 1 (the channel diameter is 0.5 mm, and the heat exchange area calculated based on the actual reaction volume is 8000 $m^2/m^3$). By adjusting and controlling the flows of isobutene and chlorine gas, the reaction residence time reaches 0.1 second. A molar ratio of the isobutylene to the chlorine gas is 1.02:1, and the reaction temperature is controlled to 30° C. by low-temperature water. After 30 minutes of stable operation, a liquid product is sampled from the outlet of the reactor, and the composition of the liquid product is analyzed as the following mass content: 88.7% of 2-methylallyl chloride, 2.1% of chloro-tert-butane, 1.5% of isobutenyl chloride, 6.0% of dichloro-tert-butane, and 1.5% of dichloro-isobutene. Therefore, the selectivity of the calculated 2-methylallyl chloride is calculated as 90.5%.

EXAMPLE 3

Isobutene and chlorine gas are introduced respectively into the microchannel reactor shown in FIG. 1 (the channel diameter is 0.4 mm, and the heat exchange area calculated based on the actual reaction volume is 10000 $m^2/m^3$). By adjusting and controlling the flows of isobutene and chlorine gas, the reaction residence time reaches 0.5 second. A molar ratio of the isobutylene to the chlorine gas is 1.01:1, and the reaction temperature is controlled to 10° C. by freezed brine. After 30 minutes of stable operation, a liquid product is sampled from the outlet of the reactor, and the composition of the liquid product is analyzed as the following mass content: 89.3% of 2-methylallyl chloride, 2.3% of chloro-tert-butane, 1.4% of isobutenyl chloride, 5.7% of dichloro-tert-butane, and 1.3% of dichloro-isobutene. Therefore, the selectivity of the calculated 2-methylallyl chloride is calculated as 91.1%.

EXAMPLE 4

Isobutene and chlorine gas are introduced respectively into the microchannel reactor shown in FIG. 2 (the channel diameter is 0.3 mm, and the heat exchange area calculated based on the actual reaction volume is 13330 $m^2/m^3$). By adjusting and controlling the flows of isobutene and chlorine gas, the reaction residence time reaches 0.3 second. A molar ratio of the isobutylene to the chlorine gas is 1.01:1, and the reaction temperature is controlled to 20° C. with low-temperature water. After 30 minutes of stable operation, a liquid product is sampled from the outlet of the reactor, and the composition of the liquid product is analyzed as the following mass content: 89.1% of 2-methylallyl chloride, 2.2% of chloro-tert-butane, 1.5% of isobutenyl chloride, 5.8% of dichloro-tert-butane, and 1.4% of dichloroisobutene. Therefore, the selectivity of the calculated 2-methylallyl chloride is calculated as 90.9%.

The invention claimed is:

1. A synthesis reactor assembly for producing high-selectivity 2-methyl-3-chloroallyl, comprising:
    an isobutylene supply having isobutylene;
    a chlorine gas supply having chlorine gas;
    a plurality of synthesis reactors arranged side-by-side, each synthesis reactor comprising:
        a synthesis reaction tube fluidly coupled with an isobutylene inlet tube configured to receive the isobutylene from the isobutylene supply and fluidly coupled with a chlorine gas inlet tube configured to receive chlorine gas from the chlorine gas supply;
        wherein the isobutylene inlet tube, the chlorine gas inlet tube, and the synthesis reaction tube are connected in tee form;
        wherein the isobutylene inlet tube and the chlorine gas inlet tube are in a U-shape, and an upper end of the synthesis reaction tube is connected to the U-shape to form the tee form; and
        wherein the isobutylene inlet tube, the chlorine gas inlet tube, and the synthesis reaction tube have a diameter of 0.2-0.5 mm, respectively;
    a cooling jacket wrapped around the plurality of synthesis reactors arranged side-by-side; and
    a cooling surface of each synthesis reactor has a heat exchange area of 8000-20000 $m^2/m^3$ based on an actual reaction volume of each synthesis reactor.

2. The synthesis reactor assembly for producing high-selectivity 2-methyl-3-chloroallyl of claim 1, comprising:
    isobutylene in each isobutylene inlet tube; and
    chlorine gas in each chlorine gas inlet tube.

3. A method for synthesizing high-selectivity 2-methyl-3-chloroallyl, comprising:
    providing the synthesis reactor assembly of claim 1;
    feeding isobutylene from the isobutylene supply through each isobutylene inlet tube and chlorine gas from the chlorine gas supply through each chlorine gas inlet tube;
    mixing the isobutylene and the chlorine gas at each tee form to produce a mixture of isobutylene and chlorine gas; and
    performing a gas-phase chlorination reaction of the mixture of isobutylene and chlorine gas in each synthesis reaction tube to produce 2-methyl-3-chloroallyl.

4. The method according to claim 3, wherein an excess amount of isobutylene is added in the chlorination reaction.

5. The method according to claim 4, wherein a molar ratio of the isobutylene to the chlorine gas is 1.005~1.02:1.

6. The method according to claim 3, wherein the chlorination reaction temperature is 0~30° C. and the chlorination reaction residence time is 0.1~1 second.

* * * * *